United States Patent [19]

Wilkins

[11] Patent Number: 4,778,465
[45] Date of Patent: Oct. 18, 1988

[54] SURGICALLY IMPLANTABLE AREOLA AND NIPPLE PROSTHESIS

[76] Inventor: Ebtisam S. Wilkins, 17009 Dace Dr., Rockville, Md. 20855

[21] Appl. No.: 58,657

[22] Filed: May 22, 1987

Related U.S. Application Data

[63] Continuation of Ser. No. 795,614, Nov. 6, 1985, abandoned, which is a continuation-in-part of Ser. No. 671,317, Nov. 14, 1984, abandoned.

[51] Int. Cl.⁴ .................................................. A61F 2/12
[52] U.S. Cl. ............................................. 623/8; 623/7
[58] Field of Search ......................................... 623/7, 8

[56] References Cited

U.S. PATENT DOCUMENTS 3,986,213 10/1976 Lynch ..................................... 623/8
4,364,880 12/1982 Howse ..................................... 623/7

FOREIGN PATENT DOCUMENTS 837000 4/1952 Fed. Rep. of Germany .......... 623/7

*Primary Examiner*—Richard J. Apley
*Assistant Examiner*—David J. Isabella

[57] ABSTRACT

A surgically implantable areola and nipple prosthesis comprising a base and a nipple forming protrusion, wherein said base is concave on one surface, and convex on the other surface and wherein the nipple forming protrusion is integrally formed onto the convex surface, and wherein the concave surface of the implantable nipple prosthesis may be affixed to a usual breast implantable sac in a location and manner so that the nipple forming prosthesis is oriented in as nearly normal position as possible, or wherein the invention may be implanted in a pocket in tissue as a separate item; and wherein the skin and tissue of the patient is closed about the areola and nipple forming prosthesis, and wherein the patient's skin will naturally assume the shape of the areola and nipple forming prosthesis, and wherein the exterior skin now shaped as an areola and nipple can be colored to resemble an areola and nipple, and wherein the coloring may be of the removable type, such as make-up, or of the more permanent type, such as dyeing or tattooing.

9 Claims, 2 Drawing Sheets

SURGICALLY IMPLANTABLE AREOLA AND NIPPLE PROSTHESIS

This application is a continuation of application Ser. No. 795,614 filed Nov. 6, 1985 now abandoned which is a continuation-in-part of Ser. No. A 671,317 filed Nov. 14, 1984 now abandoned.

SUMMARY

A great number of women have had and will have to undergo radical mastectomy which generally involves the removal of one or both breasts, incuding the areola and nipple. There have been innumerable devices invented for implant under the patients skin, most of which involve a sac containing a filler material which when implanted will give the woman patient at least the resemblance of a breast to fill a brassiere, and which will respond resiliently to pressure. However, when such a patients breast is exposed to view, it immediately becomes obvious that she has had her breast removed because there is no nipple or areola. It is therefore an objective of the invention to provide a means for forming the appearance of a nipple and areola from the skin and tissue of the patient; and when formed the patient can apply make-up or dye, or even have the areola and nipple area tattooed to ehance the natural appearance and coloration. It is also an objective of the device to make it optionally attachable to any breast implant so that the physician can artistically arrange the sac and the nipple forming prosthesis together during the implant operation into a natural appearing configuration for each individual patient.

DESCRIPTION OF THE PRIOR ART

Field of the Invention

This invention relates generally to breast implant devices, and more particularly to a breast implant prosthesis for the forming of an areola and nipple resemblance under the patients skin.

Description of the Prior Art

During a radical mastectomy, the patient's skin near the breast is generally cut from near the patients collar bone down to the area of the areola, and around the areola and tissue under the skin is remove along with the areola and nipple. After a healing period in which the excess skin is folded to the patient's chest, an implant operation may be performed in which the surgeon implants a sac under the tissue and skin of the patient causing the skin covering said sac to protrude and have the soft resilience of a natural breast. Numerous mammary prothesis have been deviced for the breast implant. FRISH, U.S. Pat. No. 4,205,401 and NAFICY, U.S. Pat. No. 4,298,998 are typical. However, these implants are breast prosthesis, and when the areola and nipple have been removed they do nothing toward aiding in the formation of a nipple-like structure in the skin of the patient.

DESCRIPTION OF THE PREFERRED EMBODIMENT

Figure 1:
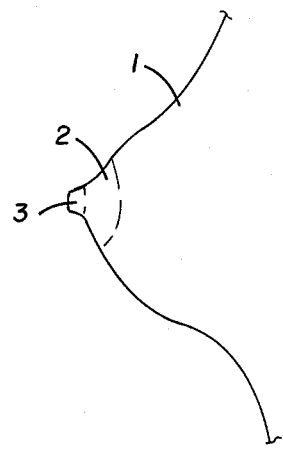
FIG. 1 is a depiction of a normal breast.
Figure 2:
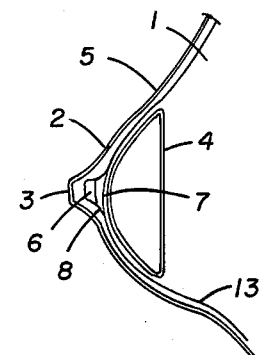
FIG. 2 is a depiction of the invention used in conjunction with a breast implant or implant sac, the invention and the implant being in separate pockets of tissue.
Figure 3:
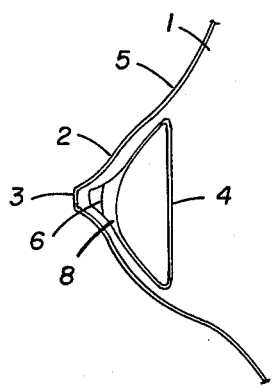
FIG. 3 is a depiction of a breast implant with the invention placed in close proximity to the breast implant in the same pocket of tissue.
Figure 4:
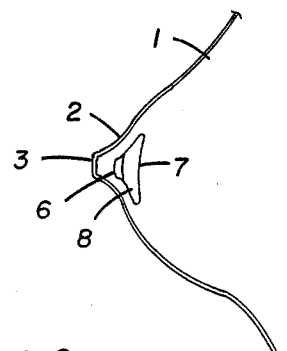
FIG. 4 is a depiction of a breast with only the invention implanted therein.

As shown in FIG. 1, a woman's breast is generally comprised of a breast proper 1, upon which at the protruding portion is the areola 2, and nipple 3. During a radical mastectomy the areola 2 and nipple 3 are removed, as well as some undelying tissue. In a routine implant procedure, a breast prosthesis, sac 4, either filled or inflatable, is implanted under the tissue 12 and skin 5, or under the muscle 13, of the patient in the breast area, and the tissue 12 and skin 5, and muscle 13 if cut, are closed and permitted to heal over the implanted sac. The implanted sac gives the breast proper 1 the approximate shape and resiliency of a natural breast. However, the breast is formed by the sac 4 lacks an areola 2 and nipple 3. The invention is shown generally in FIG. 2 to be comprised of a base 8 and the protrusion 6. The base 8 and the protrusion 6 are made integral with each other. The base 8 is shown generally to be a disk shape with a slightly concave side 7 which is shaped to the approximate curvature of the sac 4, or to the approximate curvature of the muscles 13 overlying the sac 4. The other side of the base 8 is slightly convex, as will be further described hereinafter. The protrusion 6 is shaped generally as a small cylinder whose axis is approximately orthogonal to the base 8. The invention including the base 8 and the protrusion 6 are made of biologically compatible material which is non-absorbing, soft and resilient, and which cannot be permanently deformed by pressure which would normally be applied to the breast area of a woman. Even in the event of an accident, any implantable material should not become a weapon of other dangerous device against the woman's own body; therefore, there should be no metal in the device. Metals are subject to corrosion, and can become even splinter-like if implanted in the soft tissue of a breast and not perfectly isolated from the tissue. The purpose of the invention is to provide a very small structure under the skin 5 and tissue 12 so that when the skin has grown and healed over the device, the skin 5 will have the approximate formation of an areola 2 and nipple 3. Consequently, in determining the size of the device to be implanted, consideration must be taken of the size of artificial areola 2 and nipple 3 that is desired and appropriate for the patient, as well as the thickness of the skin 5 and tissue 12 of the patient. It is obvious however that the diameter of the protrusion 6 must be small because there will be two thicknesses of skin 5 and tissue 12 on the diameter of the protrusion 6 for form the appearance of a normal nipple 3. Additionally, the height of the protrusion 6 must consider that one layer of skin 5 and tissue 12 will be on the protruding end of the protrusion 6 and care must be taken to achieve a total height in order that the artificial nipple 6 appears normal when the skin 5 has healed over the protrustion 6. Generally, a natural areola is a very slightly raised area surrounding the nipple. To give the skin 5 a very natural appearance of an areola, the base 8 has on its convex surface a slightly raised portion, designated central portion 10. This central portion 10 is the portion of the base that is the thickest, and therefore the least flexible, yet it must be easily and elastically deformed by slight pressure applied to the skin.

Figure 5:
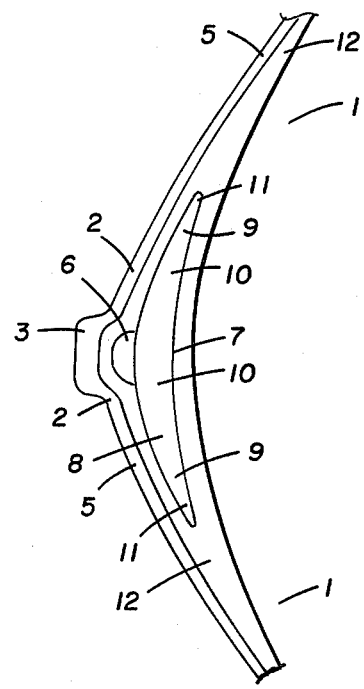
FIG. 5 is a cross section of the invention.
Figure 6:
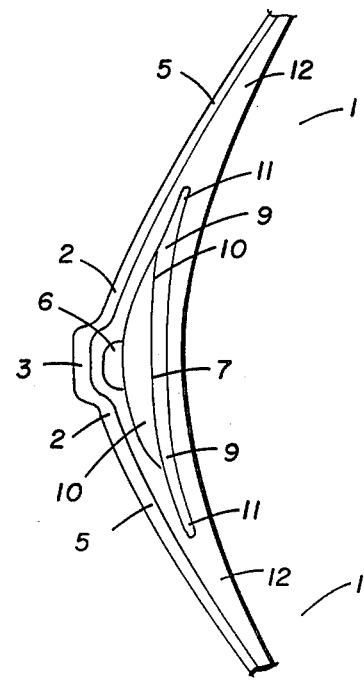
FIG. 6 is a cross section of another configuration of the invention.

5. This central portion 10 is surrounded by an annular portion 9 which is made integral with the central portion 10. The annular portion 9 is generally very thin and elastically flexible at the edges, but the edges of the annular portion 9 must not be thin, nor so rigid, as to have the characteristics of a sharp edge. Indeed, the edges of the annular portion 9 should have the resilience, rigidity, flexibility, softness as nearly as possible as that of the tissue 12. During the healing process. some degree of tissue attachment to the device is to be expected, and is desired. Two configurations of the device are shown in FIGS. 5 and 6. In FIG. 5 the base 8 is shown to have a central portion of slightly greater thickness than the annular portion 9 and the annular portion 9 is shown to be substantially thinner than the central portion 10. The juncture of the central portion 10 with the annular portion 9 is shown to be a smooth continuous line, or slightly convex curved. This smoothness in the change of thickness of the base 8 from the annular portion 9 to the central portion 10 will result in a less pronounced appearing artificial areola 2. FIG. 6 shows the juncture of the central portion 10 and the annular portion 9 to be a gradual horizontal S shaped curve and this configuration will result in a slightly more pronounced artificial areola 2.

During an implant operation, the surgeon with his considerable artistic skill, conceives the proper orientation of the sac 4 and the invention. Once the orientation of the sac 4 and the invention relative to each other have been determined. the invention is either affixed to the sac 4 in any convenient and satisfactory manner and implanted as a unit, or the invention is implanted in a pocket of tissue 12 separately. If the invention is implanted as a separate item from the sac 4, the invention is placed within a pocket within the tissue 12 and a layer of muscle and tissue 12 separate the invention from the sac 4. The patient's skin 5 and tissue 12 are closed over the implant. As the healing process associated with the implant operation progresses, the patient s skin 5 and tissue 12 will conform to the shape of the invention, producing a skin-colored raised portion in the area of the areola 2 and the nipple 3. The patient, when fully recovered, can now easily apply make-up to the raised area to simulate the natural coloring of the areola 2 and nipple 3. If more permanent coloring is desired, the patient may apply dyes or even have the areas tattooed. When the invention is implanted with a sac 4 as an attachment to the sac 4, the invention will aid in retaining the sac in the proper place, and the patient will feel much more confident and natural, and proud of her appearance, all of which will aid in the patient's recovery. However, the surgically best procedure is to implant the invention separate from the sac 4.

While the foregoing has been concerned with a reconstruction of an entire breast 1 with areola 2 and nipple 3, there are many instances when a woman needs only the areola 2 or nipple 3 or both reconstructed. Accident victims, and women with congenital deficiencies are the most obvious type patients where an entire breast 1 reconstruction would not be needed. The invention is perfectly usable by itself without a sac 4, in those instances when an entire breast 1 does not need reconstructing. As shown in FIG. 5 the invention may be implanted in the breast 1 of a woman in the tissue 12 under the skin 5. It is in this use of the invention where the necessity of the annular portion 9 being very thin, yet not shartp is most obvious. As shown in FIG. 5 the edge of the annular portion 9 must be very thin so as to not make a noticeable raised portion of the skin at a distance from the areola 2. Furthermore, it is desirable that the tissue 12 near the skin 5 not be separated from the tissue 12 underneath the base 8 for any distance from the edge of the annular portion 9. Becuse of the motion of the breast 1 due to normal activities of the woman, the edge of the annular portion must have nearly the same resilience, flexibility, softness and other physical characteristics of natural tissue and skin 5. If the edge of the annular portion 9 did not have these characteristics, the normal movement of the breast 1 and skin 5 would cause the edge of the annular portion 9 to injure the tissue and skin 5 at the edge of the annular portion 9.

Thus there are three configurations of the invention. One where the juncture of the annular portion 9 and the central portion 10 is continuous; another where the juncture of the annular portion 9 and the central portion 10 is a gradual horizontal S shaped curve, and wherein either of these configurations may be used independently without a sac 4. The third configuration is where either of the first two configurations are used in conjunction with a sac 4, either by attachment or by placement of the invention and the sac in separate tissue pockets.

In any of the three configuration the dimensions of the invention must be within certain limits, because of the geometry of a woman's breast. The protrusion 6 should be between about 0.02 centimeter to about 3.0 centimeter in diameter, and should rise above the convex surface 7 of the base by between about 0.1 centimeter to about 3.0 centimeter. The central portion 10 should be between about 0.1 millimeter to about 10.0 centimeter thick near the protrusion 3 and can gradually reduce to the edge of the annular portion 9 or it can taper radially to between about 0.1 millimeter to about 10.0 centimeter thick at the juncture of the annular portion 9 and then smoothly reduce in a horizontal S shaped curve to the edge of the annular portion 9. The edge of the annular portion 9 should thin to between about 0.1 millimeter to about 10. centimeter. The diameter of the base 8 should be between about 0.5 centimeter to about 10. centimeter while the diameter of the central portion 10 should be between about 0.2 centimeter to about 3. centimeter. Actual desired dimensions will determined by measuring the patient's normal breast, thickness of the tissue 12 and skin 5 thickness.

I claim:

1. A surgically implantable areola and nipple prosthesis for insertion under the skin proximate to the center of a breast, by means of a small incision used to form a pocket in the breast, the implant being made of a medical grade biocompatible material and held in place by said breast, said prosthesis comprising a base portion comprising a relatively thin disc having a convex side and a concave side, and said disc being tapered from its center to its edge and having a thickness of between about 0.1 millimeter to about 10 centimeters; and a diameter of between 0.5 centimeter to about 10 centimeters, and a protrusion disposed generally proximate to the center of the base, said protrusion being generally cylindrical in shape, and having a height of between about 0.1 centimeter to about 3.0 centimeters, and a diameters at said base portion of between about 0.2 centimeter to 3.0 centimeters, the protrusion having an axis which is generally orthogonal to the base portion and extending from said convex side of the base portion, said base portion having a central portion and an annular portion terminating at an edge, said central portion being thicker than the annular portion, and the annular portion gradually thinning towards the edge, the edge having physical characteristics similar to the patient's tissue, and formed of a soft, flexible, resilient material.

2. The prosthesis of claim 1 wherein the prosthesis further comprises a surgically implantable breast prosthesis implanted under muscles of the breast, said areola and nipple prosthesis being operable to be implanted under a patient's skin and over the patient's muscles.

3. The prosthesis of claim 1 wherein the central portion and the annular portion are separate members joined at a juncture.

4. The prosthesis of claim 1 wherein the central portion is generally thicker than the annular portion and is joined to the annular portion at a juncture, said juncture being in the form of a smooth and continuous curve.

5. The prosthesis of claim 1 wherein the protrusion and the base portion are made integral with each other; the shape of the base portion being one of the group consisting of circular, square, triangular, and generally complex polyhedral shapes.

6. The prosthesis of claim 1 wherein the protrusion and the base portion are made integral with each other, the cross-sectional shape of said protrusion in a plane generally parallel to the plane of said base portion being one of the group consisting of circular, square, triangular, and generally complex polyhedral shapes.

7. The prosthesis of claim 1 wherein the prosthesis comprises a shell constructed of said soft, flexible, resilient, biocompatible material filled with one of the group consisting of sterile physiological saline solution, a gel solution, a solid selected from the group consisting of silicones, polyamides, polyolefines, polyesters, cellulosic and cellulose derivative materials, fluorinated polymers, vinyls, epoxies, phenolics, collagen, and hydrogels.

8. The prosthesis of claim 1, wherein the protrusion has a tip and extends from said base portion to said tip and is tapered from the base portion toward the tip, the taper having an angle with respect to an axis of said protrusion of from about 1.0 degrees to about 45.0 degrees.

9. The prosthesis of claim 1, wherein the base portion has a diameter of between about 3.0 centimeters to about 5.0 centimeters, and wherein the protrusion comprises a tapered, generally cylindrical member extending generally orthogonally with respect to the base, and wherein the height of the protrusion is between about 0.2 centimeter to about 2.0 centimeters, and wherein the diameter of the protrusion is between about 0.5 centimeter to about 2.0 centimeters; and wherein the protrusion has a tip, and wherein the central portion has a thickness of between about 0.5 centimeter to about 1.5 centimeters, and wherein the base portion has a thickness which tapers from the center portion toward the edge, and wherein the thickness of the base portion at said edge is between about 0.05 centimeter to 0.3 centimeter.

* * * * *